United States Patent [19]

Buzza et al.

[11] Patent Number: 4,888,998
[45] Date of Patent: Dec. 26, 1989

[54] SAMPLE HANDLING SYSTEM

[75] Inventors: Edmund E. Buzza, Fullerton; Delbert D. Jackson, Brea, both of Calif.

[73] Assignee: Beckman Instruments, Inc., Fullerton, Calif.

[21] Appl. No.: 355,077

[22] Filed: May 17, 1989

Related U.S. Application Data

[63] Continuation of Ser. No. 145,695, Jan. 15, 1988, abandoned, which is a continuation of Ser. No. 884,454, Jul. 11, 1986, abandoned.

[51] Int. Cl.$^4$ .............................................. B01L 3/02
[52] U.S. Cl. ................................ 73/864.21; 73/864.22
[58] Field of Search ........... 73/864.11, 864.12, 864.14, 73/864.15, 864.21, 864.22, 864.25, 864.34, 864.81, 864.83, 864.84, 864.85, 864.23; 422/81, 100; 204/400, 409; 222/148

[56] References Cited

U.S. PATENT DOCUMENTS

| | | | |
|---|---|---|---|
| 3,186,799 | 6/1965 | Hach | 422/81 |
| 3,327,520 | 6/1967 | Stapp, Jr. | 73/23.1 |
| 3,604,267 | 9/1971 | Johns | 73/422 |
| 3,719,086 | 3/1973 | Bannister et al. | 73/864.22 |
| 3,787,291 | 1/1974 | Deuringer et al. | 204/409 |
| 3,788,816 | 1/1974 | Rohrbaugh et al. | 23/253 |
| 3,869,068 | 3/1975 | Chen | 222/148 |
| 3,902,371 | 9/1975 | Hooper et al. | 73/864.24 |
| 3,911,749 | 10/1975 | Hendry | 73/864.22 |
| 3,964,864 | 6/1976 | Dahms | 23/230 |
| 3,997,420 | 12/1976 | Buzza | 204/195 |
| 4,019,861 | 4/1977 | Dahns | 422/83 |
| 4,086,061 | 3/1978 | Hoffa et al. | 23/259 |
| 4,140,018 | 2/1979 | Maldarelli et al. | 73/864.25 |
| 4,170,523 | 10/1979 | Buzza et al. | 204/1 |
| 4,199,988 | 4/1980 | Riegger | 73/863.81 |
| 4,202,747 | 5/1980 | Buzza et al. | 204/195 |
| 4,218,197 | 8/1980 | Meyer et al. | 417/442 |
| 4,259,289 | 3/1981 | Curry et al. | 73/864.25 |
| 4,297,903 | 11/1981 | Buzza | 73/864.22 |
| 4,463,615 | 8/1984 | Buzza | 73/863.32 |
| 4,490,234 | 12/1984 | Buzza | 204/409 |
| 4,621,534 | 11/1986 | Munari et al. | 73/864.86 |
| 4,705,667 | 11/1987 | Marsoner et al. | |

FOREIGN PATENT DOCUMENTS

| | | |
|---|---|---|
| 3502546A1 | 1/1985 | Fed. Rep. of Germany . |
| 2025900 | 1/1980 | United Kingdom . |

*Primary Examiner*—Robert R. Raevis
*Attorney, Agent, or Firm*—William H. May; Arnold Grant; Gary T. Hampson

[57] ABSTRACT

A sample handling system including a sample injection cell having an open chamber in turn comprising an upper portion for washing a sample handling probe and a lower portion adapted to reeive the probe for injection of a sample and fluid mixture into a flow analysis device. The cell enables the probe to be withdrawn from the cell and moved to other analysis modules for injection of sample therein. The cell includes a seal between the upper portion and lower portion of the chamber and the probe includes a mating seal near the tip of the probe. A plurality of conduits are formed into the cell for flowing sample and a fluid such as diluent through the cell to a flow analysis device and for filling the cell for washing the probe tip.

14 Claims, 2 Drawing Sheets

SAMPLE HANDLING SYSTEM

This application is a continuation of co-pending application Ser. No. 145,695, filed on Jan. 15, 1988 (now abandoned), which was a continuation of application Ser. No. 884,454 filed on July 11, 1986 (now abandoned).

BACKGROUND

The present invention relates generally to the field of automated analytical instruments and, more particularly, to a system of sample handling for automated clinical chemistry analyzers.

The Astra ® System and the E4A ™ Analyzer (available from Beckman Instruments, Inc., Brea, California) are clinical chemistry analyzers that illustrate two different types of analytical methodologies each having certain desirable attributes and advantages. The Astra Analyzer may include a plurality of individual analysis modules each having an open reaction cup. An automated sample probe withdraws a sample volume from samples carried on a carousel and distributes the sample volume to the analysis modules in accordance with the tests selected by the instrument operator.

The E4A Analyzer, on the other hand, utilizes a flow cell through which sample and diluent flow for the determination of four "electrolytes", namely, sodium, potassium, chloride and $CO_2$. The analyzer includes a shear valve (disclosed in U.S. Pat. No. 4,297,903) having a bottom portion that swings to the side, allowing a sample pickup probe to extend vertically through the shear valve to aspirate sample from a cup aligned with the probe. The tip of the probe is withdrawn into the shear valve and the lower portion of the valve closes. Diluent from a diluent source flows into the valve, is mixed with the sample from the probe and flows to a flow analysis module.

The Astra Analyzer modules and the E4A Analyzer flow technology each provide unique advantages in the analysis of patient samples. For example, the Astra Analyzer enables the parallel analysis of samples using incompatible reagents that could not be used in a flow analysis module. On the other hand, the E4A Analyzer provides simplified fluid handling and minimizes reagent consumption. Although it would be desirable to combine such analytical modules and the flow analysis technology, the shear valve of the E4A Analyzer allows only for vertical displacement of the probe. The probe cannot be removed from the shear valve. Also, the shear valve includes a seal around the probe and a seal between the bottom and stationary portions of the valve, both of which are subject to wear during operating cycles of the E4A Analyzer.

Thus, while it is desirable to combine the analysis module and flow analysis technologies, the sample withdrawal, injection and dilution required for the flow analysis technology has been incompatible with the sample probe pickup and horizontal movement required to provide sample volumes to separate analysis modules.

SUMMARY OF THE INVENTION

The present invention solves the problem posed by the prior art, providing a sample handling system that allows the integration of separate analysis modules with a flow analysis technique.

In accordance with the present invention, a sample handling system includes a sample injection cell and a probe adapted to carry fluid. The sample injection cell includes a body having a chamber adapted to receive the probe. The chamber includes an open-ended upper portion and closed-ended lower portion. The probe may be inserted into both the upper and lower portions of the sample injection cell. Sealing means is disposed in the lower portion of the chamber for sealing the tip of the probe so that the tip and the lower portion can together cooperate to define an enclosed space suitable for fluid pressurization and fluid flow. A plurality of lower conduits communicate with the lower portion of the chamber.

The upper portion of the chamber may be tapered for guiding the probe tip into the lower portion of the chamber and the sealing means may include an annular seal near the tip of the probe and a second annular seal between the upper and lower portions of the chamber. The inside diameter of the second seal is greater than the outside diameter of the probe so that the second seal is not worn by insertion and removal of the probe into the lower chamber. The system may further include control means for inserting the probe tip into the lower portion of the chamber to press the first and second seals together so as to seal the probe tip within the chamber lower portion.

An upper conduit may communicate with the upper portion of the chamber and the control means may also be for inserting the probe tip into the upper portion of the chamber for washing the probe tip.

The system may further include fluid supply means connected to one of the lower of conduits and adapted to provide wash fluid into the chamber with excess wash fluid being drawn from the upper conduit. The system may also include a plurality of sample analyzing means each adapted to accept and analyze fluid deposited by the probe and flow analyzing means in fluid communication with one of the lower conduits for analyzing fluids injected into the cell from the probe. One of the lower conduits may also be in fluid communication with diluent pumping means for pumping diluent simultaneously with sample injection into the lower portion of the chamber whereupon the diluted sample flows into the flow analyzing means for analysis.

DETAILED DESCRIPTION

Figure 1:
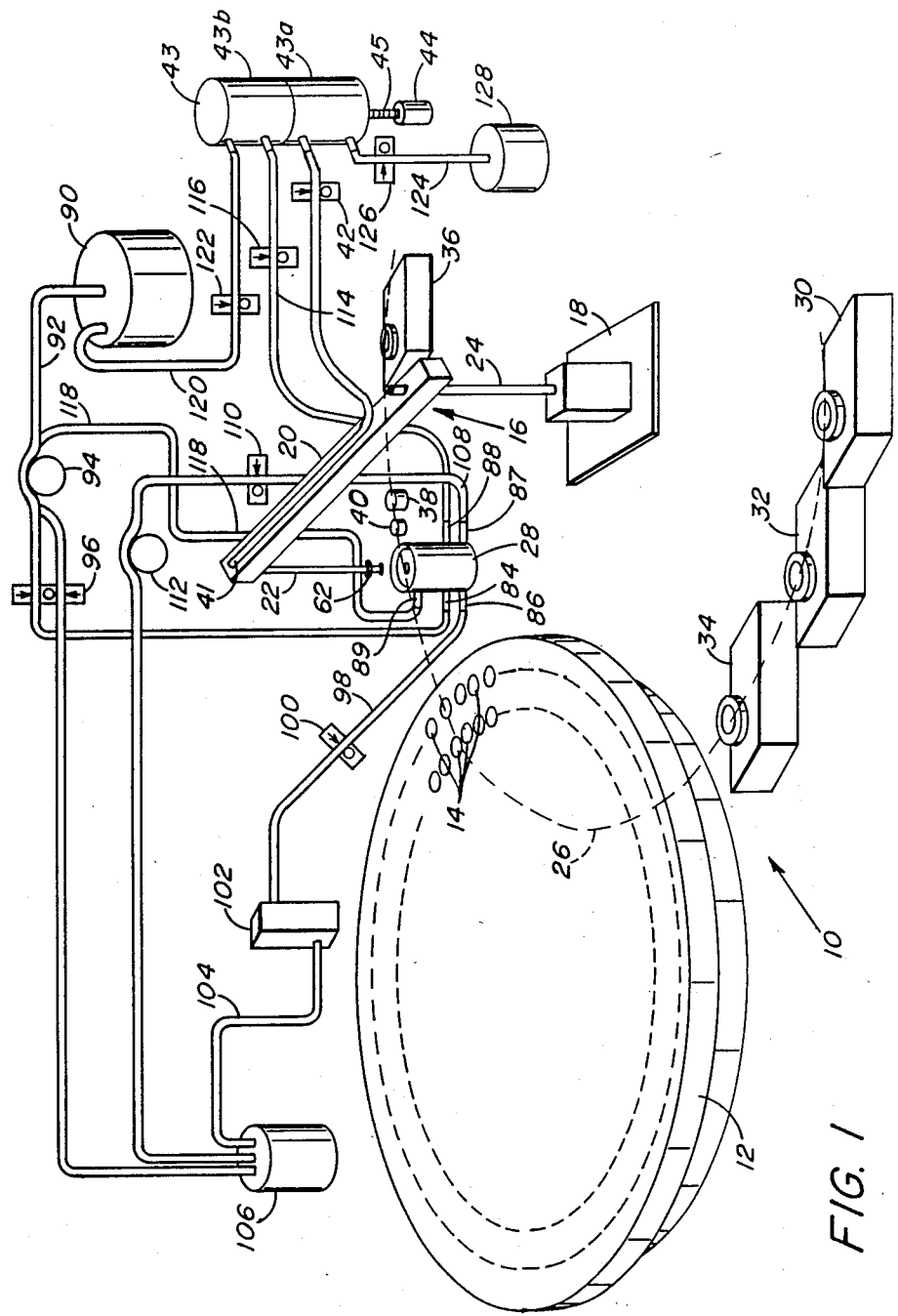
FIG. 1 is a simplified diagram of a sample handling system in accordance with the present invention.

With reference to FIG. 1, a sample handling system in accordance with the present invention is included as part of an analyzer 10 showed in simplified form. The analyzer 10 includes a sample carousel 12 including a plurality of sample carrying locations 14 disposed in circular rows near the periphery of the sample carousel 12. The sample carousel 12 is rotatably supported at its center and may include a suitable stepper motor and control systems to rotate the sample carousel 12 as is known in the art.

The analyzer 10 also includes a sample probe assembly 16 comprising a displacement mechanism 18, radial support arm 20 and a fluid aspirating and dispensing probe 22. The displacement mechanism 18 includes a vertical shaft 24 which can be raised and lowered and rotated about its central axis, again using suitable motors and control techniques well known in the automated instrument art. The shaft 24 is affixed to one end of the support arm 20, thus enabling the support arm 20 and probe 22 fixed to the other end of the arm 20 to be raised and lowered and rotated such that the tip of the probe is adapted to travel in a path over an arc 26.

The arc 26 passes over the inner and outer rows of sample carrying locations 14 as well as over a sample injection cell 28, four analysis modules 30, 32, 34, 36, and two calibrator cups 38 and 40. The modules 30, 32, 34, 36 may be similar to modules used on the Astra Analyzer mentioned above or other suitable single analyte modules otherwise well known in the art. In the embodiment disclosed herein, the modules 30, 32, 34, 36 are adapted for the analysis of glucose, BUN, calcium and creatinine. The calibration cups 38 and 40 may contain calibration substances required for the periodic calibration of the analyzer 10 and dispensed via the probe 22.

The probe 22 is connected by conduit 41 through a pinch valve 42 to a first chamber 43a of a suitable displacement pump 43 adapted to aspirate fluid such as samples contained in the locations 14 into the probe 22 and subsequently dispense such fluid into the analysis modules 30, 32, 34, 36 or the sample injection cell 28. The pump 43 is actuated by a stepper motor 44 acting through a lead screw 45 which in turn displaces a piston within the chamber 43a, all in a conventional fashion.

Figure 2:
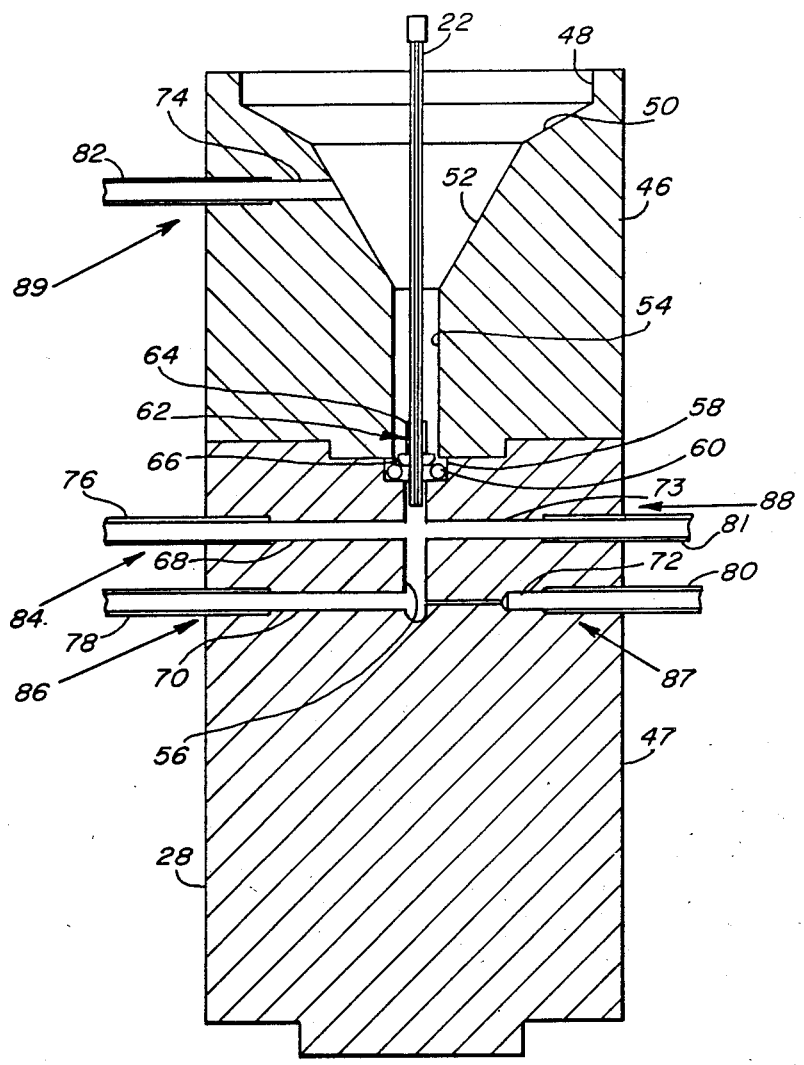
FIG. 2 is a cross-section view of a sample injection cell used in the sample handling system of FIG. 1.

The sample injection cell 28 and probe 22 tip are illustrated in more detail with reference to FIG. 2 which shows a cross-section view of the cell 28. The cell 28 is of a generally cylindrical external configuration and may be formed from an upper body 46 and a lower body 47 secured by means of suitable fasteners such as screws (not shown in the view of FIG. 2). The upper body 46 includes an opening 48 at the top thereof axially aligned with the upper body 46 and having a diameter slightly less than the diameter of the cell 28 and about ten times the outside diameter of the probe 22. The lower portion of the opening 48 joins a first tapered surface 50 which in turn joins a second tapered surface 52. The surface 50 tapers more rapidly than the surface 52 with the tapered surface 52 joining a cylindrical passage 54 having a diameter slightly larger than the outside diameter of the probe 22 and a seal 62 (described below).

The lower body 47 includes a vertical hole 56 and an annular space 58 at the top of the hole 56 which receives an O-ring seal 60. The opening 48, tapered surfaces 50, 52, cylindrical passage 54, vertical hole 56, space 58 and O-ring 60 are all coaxially aligned with the central axis of the cell 28. The tapered surfaces 50 and 52 help to guide the probe 22 as the tip thereof is inserted into the cell 28. The diameter of the cylindrical passage 54 is slightly less than the diameter of the annular space 58 to thus clamp the O-ring seal 60 in the annular space 58 when the upper and lower bodies 46 and 47 are assembled as shown in FIG. 2.

The probe 22 includes a seal 62 near the probe tip. The seal 62 includes a cylindrical upper portion 64 which broadens to form a cone-shaped tip 66 at the lower end of the seal 62. The cone-shaped tip 66 is adapted to be urged against the O-ring seal 60 to seal the tip of the probe 22 within the vertical hole 56.

The cell 28 includes five fluid carrying bores 68, 70, 72, 73, 74 formed generally radially therein. The first bore 68 intersects the vertical hole 56 slightly below the position that the tip of the probe 22 occupies when the seals 60 and 62 are urged together as described above. The second and third bores 70 and 72 intersect the bottom of the vertical hole 56. The fourth bore 73 intersects the vertical hole 56 opposite from the first bore 68. The fifth bore 74 intersects the second tapered surface 52 slightly below the intersection of the first and second tapered surfaces 50 and 52. Each of the bores 68, 70, 72, 73, 74 is enlarged slightly near the outer cylindrical surface of the cell 28 and respective first through fifth short rigid tubing lengths 76, 78, 80, 81, 82 are pressed into the enlarged portions. The tubing lengths 76, 78, 80, 81, 82 define a fill port 84, a flow analyzer port 86, a drain port 87, a diluent port 88, and a sip port 89.

With reference now particularly to FIG. 1, the sample injection cell 28 is connected to fluid systems in the analyzer 10 which deliver diluent to the cell 28, connect the cell 28 to a low analysis device, and enable the cell 28 to serve as a washing station for the tip of the probe 22. A reservoir 90 holds a solution suitable for diluent and wash purposes and is connected via a conduit 92 through a peristaltic pump 94 and a pinch valve 96 to the fill port 84. The flow analyzer port 86 is connected via conduit 98 through a pinch valve 100 to a flow analysis device 102. The output of the flow analysis device 102 is in turn connected by a conduit 104 to a waste reservoir 106. The flow analysis device 102 may include additional reagent delivery circuits and ion selective electrodes for the analysis of chloride, sodium, potassium and $CO^2$ and is essentially identical to the flow analysis device included in the E4A Analyzer from Beckman Instruments, Inc., Brea, California, and as described in "Beckman System E4A ™ Operating Manual" (Beckman instructions number 015-556855-A), although other flow analysis devices would also be applicable. The drain port 87 is connected via a conduit 108 through a pinch valve 110 and peristaltic pump 112 to the waste reservoir 106.

The diluent port 88 is connected via a conduit 114 through a pinch valve 116 to a second chamber 43b of the pump 43. The sip port 89 is connected via a conduit 118 through the peristaltic pump 94 and the pinch valve 96 to the waste reservoir 106. The second chamber 43b of the pump 43 is also connected via a conduit 120 and pinch valve 122 to the wash/diluent reservoir 90 and the first chamber 43a is connected via a conduit 124 and pinch valve 126 to a reference solution reservoir 128.

In the operation of the analyzer 10, the sample injection cell 28 advantageously enables the flow analysis device 102 to be used simultaneously with analysis modules 30, 32, 34, 36. In an initial state, pinch valves 42, 100, and 122 are open and pinch valves 96, 110, 116 and 126 are closed. The sample probe assembly 16 is controlled to position the probe 22 over one of the sample carrying locations 14. The probe 22 is lowered into the sample carrying location 14 and pump 43 is operated to aspire a predetermined volume of sample into the probe 22 while diluent is drawn into the second chamber 43b of the pump 43. The probe 22 is raised and rotated to a position over the sample injection cell 28.

The probe 22 is lowered into the sample injection cell 28 until the seals 60 and 62 engage. Pinch valve 122 is closed, valve 116 is opened and the pump stepper motor 44 is reversed. Sample is expelled from the probe 22 into the vertical hole 56 simultaneously as diluent is delivered from the second chamber 43b through the diluent port 88, forcing the combined sample and diluent mixture through the flow analysis port 86 and the open pinch valve 100 to the flow analysis device 102.

With sample and diluent within the flow analysis device 102, the pump stepper motor 44 stops, terminating sample injection from the probe 22. Pinch valves 100 and 116 are closed, pinch valve 122 is opened, and the probe 22 is raised and rotated to the modules 30, 32, 34, 36 to inject sample volumes into each of such modules by operating the pump stepper motor 44. Currently, analyses are performed in the flow analysis device 102 and the modules 30, 32, 34, 36.

With sample delivered to all the modules 30, 32, 34, 36, the probe 22 is returned to its position above the flow cell 28. The pinch valve 96 opens both conduits 92 and 118 and the pump 94 operates to flow wash/diluent solution through the ports 84, 89 and the cell 28. The probe 22 is lowered such that the tip of the probe, contaminated with reagents from, for example, the module 36, is washed by the flow of fluid through the fill port 84, the area within the cylindrical surface 54 and the area within the tapered surface 52.

With the external surfaces of the probe tip clean, the pump 94 operation terminates and pinch valve 96 closes. Pinch valve 110 is opened and pump 112 operates to drain the cell 28 through the drain port 87. The pump 112 operation terminates, pinch valve 110 closes, and the probe 22 is lowered further into the cell 28 such that the seal 62 seats against the O-ring seal 60. Pinch valve 126 opens, pinch valve 42 closes, and the pump motor 44 operates to draw reference solution from the reservoir 128 into the first chamber 43a. Pinch valves 122 and 126 close, pinch valves 42, 100 and 116 open, and the pump motor 44 operates to pump reference solution through the probe 22 while diluent is pumped through the diluent port 88. The mixture flows to the flow analysis device 102 to clean the device and provide a reference for the device 102 prior to the next patient sample analysis. The pump motor 44 is turned off and the flow of the reference solution and the diluent accordingly terminates. The probe 22 is withdrawn from the cell 28 and moved to a sample aspiration position over the sample turntable 12. Pinch valve 116 closes and pinch valve 122 opens, readying the system for the next cycle.

Thus, the sample injection cell 28 provides a unique interface between the flow analysis device 102 and the analysis modules 30, 32, 34, 36, enabling the analyzer 10 to advantageously utilize both technologies. Furthermore, a pause otherwise required in the operation of the flow analysis device 102 while sample analysis is occurring and before the reference solution is delivered enables the probe 22 to distribute sample to the analysis modules 30, 32, 34, 36, further increasing throughput of the analyzer 10.

Although the sample injection cell 28 has been described as including fill and sip ports 84 and 89 for washing the probe 22 within the cell 28, the fill and sip ports 84 and 89 can be eliminated along with the corresponding bores 68 and 74 and a separate wash cup or cell can be connected to the conduits 92 and 118. The probe may accordingly be washed in the separate wash cup and the sample injection cell 28 used only for sample and reference injection and dilution as described above. Furthermore, the diluent in the reservoir 90 may be replaced by a reagent if required by the particular type of flow analysis device used. Thus, the sample would be mixed with the reagent and delivered to the flow analysis device. In either instance, the sample injection cell 28 is used for sample injection and mixing prior to delivery to the flow analysis device.

It will be recognized by those skilled in the art that the invention of the present application is not to be limited to the particular embodiment disclosed herein but is to be afforded the full scope of the claims appended hereto.

What is claimed is:

1. A sample handling system, comprising:
   a moveable fluid delivery probe having a tip and a sealing surface proximate the tip;
   a sample carrying location;
   a sample injection cell comprising
   a body having a chamber adapted to receive the probe, the chamber including an open end and a closed end, a first portion of the chamber proximate the open end being sized to freely receive the probe tip and the sealing surface carried by the probe;
   sealing means disposed between the first portion of the chamber and a second portion of the chamber for engaging the sealing surface carried by the probe and sealing the probe tip within the second portion of the chamber; and
   at least two conduits in communication with the second portion of the chamber;
   the system further including displacement means for moving the probe to the sample carrying location, inserting the probe tip into the sample carrying location, removing the probe tip from the sample carrying location, moving the probe to the sample injection cell, inserting the probe tip into the sample injection cell until the probe tip is in the second portion of the chamber and the sealing surface engages and seals against the sealing means, and removing the probe and probe tip from the sample injection cell.

2. A system as in claim 1 wherein the first portion of the chamber includes wall means tapering from the open end of the chamber toward the sealing means for guiding the probe toward engagement of the sealing surface and the sealing means.

3. A system as in claim 1 wherein the probe includes a first annular seal proximate the tip thereof, the first annular seal defining the sealing surface, and the sealing means comprises a second annular seal disposed between the first and second portions of the chamber, the inside diameter of the second annular seal being greater than the outside diameter of the probe tip.

4. A system as in claim 1 wherein the sample injection cell further includes a conduit in communication with the first portion of the chamber and the system further includes pump means for pumping fluid through the chamber via the conduit in communication with the first portion of the chamber and one of the conduits in communication with the second portion of the chamber.

5. A system as in claim 1 wherein the probe sealing surface has a diameter greater than the outside diameter of the probe tip.

6. A sample handling system, comprising:
   a fluid delivery probe having a tip and a sealing surface proximate the tip;
   a sample injection cell comprising
   a body having a chamber adapted to receive the probe, the chamber including an open end and a closed end, a first portion of the chamber proximate the open end being sized to freely receive the probe tip and the sealing surface carried by the probe;

sealing means disposed between the first portion of the chamber and a second portion of the chamber proximate the closed end for engaging the sealing surface carried by the probe and sealing the probe tip within the second portion of the chamber;

a conduit in communication with the first portion of the chamber; and at least two conduits in communication with the second portion of the chamber;

the system further including a plurality of sample analyzing means each adapted to accept and analyze fluid deposited in said sample analyzing means by the probe and flow analyzing means in fluid communication with one of the conduits in communication with the second portion of the chamber for analyzing fluids injected into the second portion of the chamber from the probe.

7. A system as in claim 6 wherein the system includes control means for inserting the probe tip into the first portion of the chamber, and for inserting the probe tip through the first portion of the chamber and into the second portion of the chamber and for engaging the sealing surface by the sealing means.

8. A system as in claim 7 wherein the first portion of the chamber includes walls tapering from the open end of the chamber toward the sealing means for guiding the probe toward engagement of the sealing surface and the sealing means.

9. A sample handling system comprising:
a fluid delivery probe having a tip and a sealing surface proximate the tip;
a sample injection cell comprising
a body having a chamber adapted to receive the probe, the chamber including an open end and a closed end, a first portion of the chamber proximate the open end being sized to freely receive the probe tip and the sealing surface carried by the probe;
sealing means disposed between the first portion of the chamber and a second portion of the chamber proximate the closed end for engaging the sealing surface carried by the probe and sealing the probe tip within the second portion of the chamber;
a conduit in communication with the first portion of the chamber;
at least two conduits in communication with second portion of the chamber;
the system further including control means (a) for inserting the probe tip into the first portion of the chamber, and (b) for inserting the probe tip through the first portion of the chamber and into the second portion of the chamber and for engaging the sealing surface by the sealing means;
pump means for pumping fluid through the chamber via one of the conduits in fluid communication with the second portion of the chamber and the conduit in communication with the first portion of the chamber;
fluid pumping means for pumping fluid through a second one of the at least two conduits when the probe tip is sealed within the second portion of the chamber; and
a plurality of sample analyzing means each adapted to accept and analyze fluid deposited in said sample analyzing means by the probe and flow analyzing means in fluid communication with one of the conduits in communication with the second portion of the chamber for analyzing fluids injected into the second portion of the chamber from the probe.

10. A sample injection cell for use with a fluid delivery probe and means for moving the probe relative to the cell, the fluid delivery probe including a tip and a sealing surface proximate the tip, the cell comprising:
a body having a chamber adapted to receive the probe, the chamber including an open end, a closed end, a first portion of the chamber proximate the open end, and a second portion of the chamber proximate the closed end;
a resilient annular seal disposed between the first portion of the chamber and the second portion of the chamber and adapted for engaging the sealing surface carried by probe, the inside diameter of the annular seal being greater than the outside diameter of the probe tip, the first portion of the chamber including a generally conical wall and a cylindrical wall, the conical wall having a large diameter end proximate the open end of the chamber, and a small diameter end, and the cylindrical wall of the chamber being intermediate the small diameter end and the annular seal;
a conduit in communication with the first portion of the chamber; and
at least two conduits in communication with the second portion of the chamber.

11. A sample handling system, comprising:
a fluid delivery probe having a tip and a first annular seal proximate the tip;
a sample injection cell comprising:
a body having a chamber adapted to receive the probe, the chamber including an open end and a closed end, a first portion of the chamber proximate the open end being sized to freely receive the probe tip and the first annular seal;
a second annular seal disposed between the first portion of the chamber and a second portion of the chamber proximate the closed end and adapted for engaging the first annular seal when the probe tip is within the second portion of the chamber, the inside diameter of the second annular seal being greater than the outside diameter of the probe tip;
a conduit in communication with the first portion of the chamber; and
at least two conduits in communication with the second portion of the chamber;
the system further including control means (a) for inserting the probe tip into the first portion of the chamber, and (b) for inserting the probe tip through the first portion of the chamber and the second annular seal and for pressing the first and second annular seals together to form a seal therebetween;
a plurality of sample analyzing means each adapted to accept and analyze fluid deposited in said sample analyzing means by the probe; and
flow analyzing means in fluid communication with one of the conduits in communication with the second portion of the chamber for analyzing fluids injected into the second portion of the chamber from the probe.

12. A system as in claim 11 further including fluid pumping means for pumping fluid through a second one of the at least two conduits when the probe tip is sealed within the second portion of the chamber.

13. A sample handling system, comprising:
a moveable fluid delivery probe having a tip and a sealing surface proximate the tip;
a sample injection cell comprising
a body having a chamber adapted to receive the probe, the chamber including an open end and a closed end; a first portion of the chamber proximate the open end being sized to freely receive the probe tip and the sealing surface carried by the probe;
sealing means disposed between the first portion of the chamber and a second portion of the chamber proximate the closed end for engaging the sealing surface carried by the probe and sealing the probe tip within the second portion of the chamber and
at least two conduits in communication with the second portion of the chamber;
the system further including displacement means for inserting the probe tip into the sample injection cell until the probe tip is in the second portion of the chamber and the sealing surface engages and seals against the sealing means, and for removing the probe from the sample injection cell.
a plurality of sample analyzing means each adapted to accept and analyze fluid deposited in said sample analyzing means by the probe, the displacement means further includes means for moving the probe to deposit fluid from the probe into the sample analyzing means; and
flow analyzing means in fluid communication with one of the conduits in communication with the second portion of the chamber for analyzing fluids injected into the second portion of the chamber from the probe.

14. A sample injection cell for use with a fluid delivery probe and probe moving means for moving the probe relative to the cell, the fluid delivery probe including a tip and a sealing surface proximate the tip, the cell comprising:
a body having a chamber adapted to receive the probe, the chamber including an open end, a closed end, and a second portion of the chamber proximate the closed end;
a resilient annular seal retained within the chamber and disposed between the first portion of the chamber and the second portion of the chamber and adapted for engaging the sealing surface carried by the probe and sealing the probe tip within the second portion of the chamber, the inside diameter of the annular seal being greater than the outside diameter of the probe tip, the first portion of the chamber including a generally conical wall tapering from a diameter defined by the open end of the chamber toward the annular seal;
a conduit in communication with the first portion of the chamber; and
at least two conduits in communication with the second portion of the chamber.

* * * * *

UNITED STATES PATENT AND TRADEMARK OFFICE
CERTIFICATE OF CORRECTION

PATENT NO. : 4,888,998

DATED : 12/26/89

INVENTOR(S) : Buzza et al.

It is certified that error appears in the above-identified patent and that said Letters Patent is hereby corrected as shown below:

Column 4, line 18 reads " -- the cell 28 to a low analysis device --" should read "-- the cell 28 to a flow analysis device, --"

Signed and Sealed this

Eighteenth Day of June, 1991

Attest:

HARRY F. MANBECK, JR.

Attesting Officer

Commissioner of Patents and Trademarks